US 6,572,544 B1

(12) United States Patent
Carter

(10) Patent No.: US 6,572,544 B1
(45) Date of Patent: Jun. 3, 2003

(54) BODY MONITORING APPARATUS

(75) Inventor: Hugh Carter, Edinburgh (GB)

(73) Assignee: Reynolds Medical Limited (GB)

( * ) Notice: Subject to any disclaimer, the term of this patent is extended or adjusted under 35 U.S.C. 154(b) by 202 days.

(21) Appl. No.: 09/693,283

(22) Filed: Oct. 19, 2000

(51) Int. Cl.⁷ ............................................... A61B 5/00
(52) U.S. Cl. ........................ 600/300; 600/513; 600/528; 607/5; 607/6; 607/18
(58) Field of Search .................... 600/513, 528, 600/523, 524; 607/5, 6, 18

(56) References Cited

U.S. PATENT DOCUMENTS

| | | | |
|---|---|---|---|
| 3,913,567 A | 10/1975 | Streckmann | |
| 3,921,147 A | 11/1975 | Fuhr et al. | |
| 4,183,354 A | 1/1980 | Sibley et al. | |
| 4,535,783 A | 8/1985 | Marangoni | |
| 5,012,411 A | * 4/1991 | Policastro et al. | 364/413.06 |
| 5,181,521 A | 1/1993 | Lemelson | |
| 5,474,090 A | 12/1995 | Begun et al. | |
| 5,579,775 A | * 12/1996 | Dempsey et al. | 128/670 |
| 5,701,894 A | 12/1997 | Cherry et al. | |
| 5,720,770 A | * 2/1998 | Nappholz et al. | 607/30 |

FOREIGN PATENT DOCUMENTS

| | | | |
|---|---|---|---|
| EP | 0101870 | 7/1983 | ............ A61B/5/04 |
| EP | 0101870 A3 | 9/1986 | |
| JP | 6343612 | 12/1994 | |

OTHER PUBLICATIONS

First page—Windows, Abstract: JP6343612, 2 pages.

* cited by examiner

Primary Examiner—Hieu T. Vo
Assistant Examiner—Johnny H. Hoang
(74) Attorney, Agent, or Firm—Blakely Sokoloff Taylor & Zafman

(57) ABSTRACT

ECG recording apparatus 1 includes a port 2 for connection to ECG electrodes and a microphone 3 for detecting vocal signals, Processing electronics store a recording of the vocal signals and the physiological data on the storage medium 4.

28 Claims, 2 Drawing Sheets

BODY MONITORING APPARATUS

Figure 1:
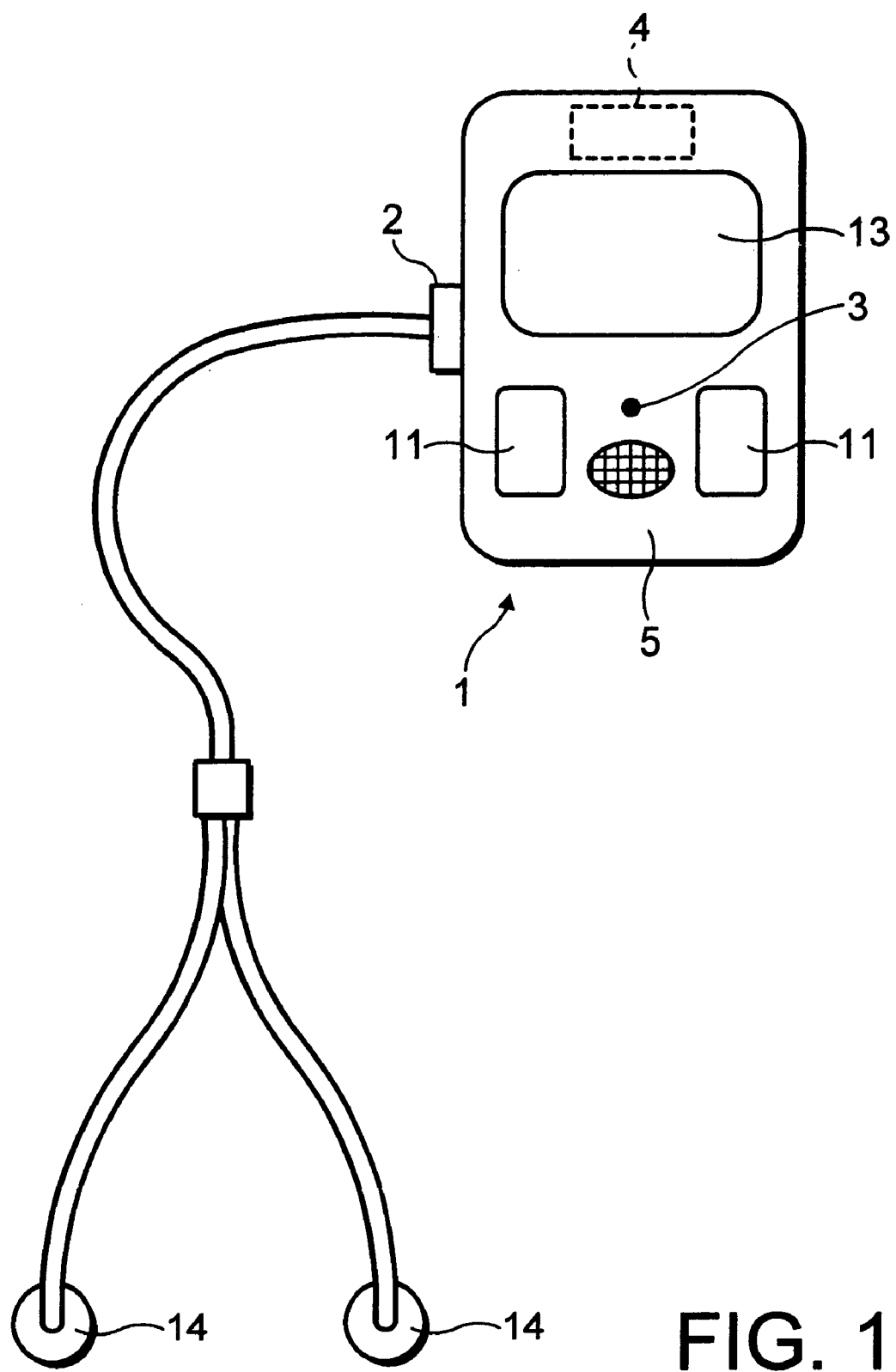

This invention relates to apparatus for recording physiological information, and more particularly to ECG recording apparatus which stores a recording of a vocal signal and physiological information.

Body monitoring apparatus generally includes physiological sensors, a monitoring device and cables connecting the sensors to the monitoring device. The sensors are attached to a patient's body to detect physiological signals and may be, for example, electrocardiogram (ECG) electrodes, electroencephalogram (EEG) electrodes or blood oxygen sensors. For example, in ECG monitoring apparatus an electrocardiogram signal is measured as the difference in potential between a set of electrodes placed externally on the body of the patient. This allows the cardiac activity to be measured.

In ambulatory monitoring the complete electronic apparatus is miniaturised and battery operated, adapted for wearing on the patient's body. WO/94/26164 describes one known ambulatory monitoring apparatus, and is incorporated herein by reference.

U.S. Pat. No. 5,314,389 disclosed an ECG monitor that gives the user an audible indication of pulse rate. U.S. Pat. No. 5,474,090, U.S. Pat. No. 4,535,783, U.S. Pat. No. 4,183,354, U.S. Pat. No. 4,087,840 and U.S. Pat. No. 3,651,280 disclose monitoring systems that record physiological information and voice information.

It is advantageous to be able to identify data which relates to the recording of the physiological information. For example, to identify the recording and any relevant details such as the patient, medication, symptoms, and to identify the clinician.

According to a first aspect of the present invention, there is provided body monitoring apparatus including: processing electronics for receiving physiological information from physiological sensors connected to the apparatus; and a sensor for detecting a sound signal; wherein the processing electronics are adapted to store a recording of a sound signal received by the sensor and a recording of physiological information, said sound signal including a component for identifying the physiological information recording to a receiving station.

The apparatus may include a loudspeaker, the processing electronics for replaying through the loudspeaker a sound signal recording stored on the storage medium. This advantageously allows the clinician to listen to any vocal recording made on the apparatus, which may then be re-recorded if necessary.

The processing electronics may be adapted for supplying power to activate the sound sensor and/or restrict power to deactivate the sound sensor, for example, in response to user commands received through an interface. This allows the power supply to be conserved.

According to a second aspect of the present invention, there is provided a method of monitoring physiological information, the method including: detecting a sound signal using a sound sensor; storing a recording of the sound signal on a data storage medium; detecting physiological information; and storing a recording of the physiological information on a data storage medium, said sound signal including a component for identifying the physiological information recording to a receiving station.

According to a third aspect of the invention, there is provided a method of monitoring patient physiological information, the method including:

storing patient physiological data from physiological sensors;

storing a sound signal capable of identifying the nature of patient physiological data to a remote receiving station;

transmitting the stored sound signal and patient physiological data to the remote receiving station; and at said remote receiving station interpreting said sound signal to identify the nature of said patient physiological data so that the data can be processed in a manner selected according to the nature of the patient's physiological data.

Figure 2:
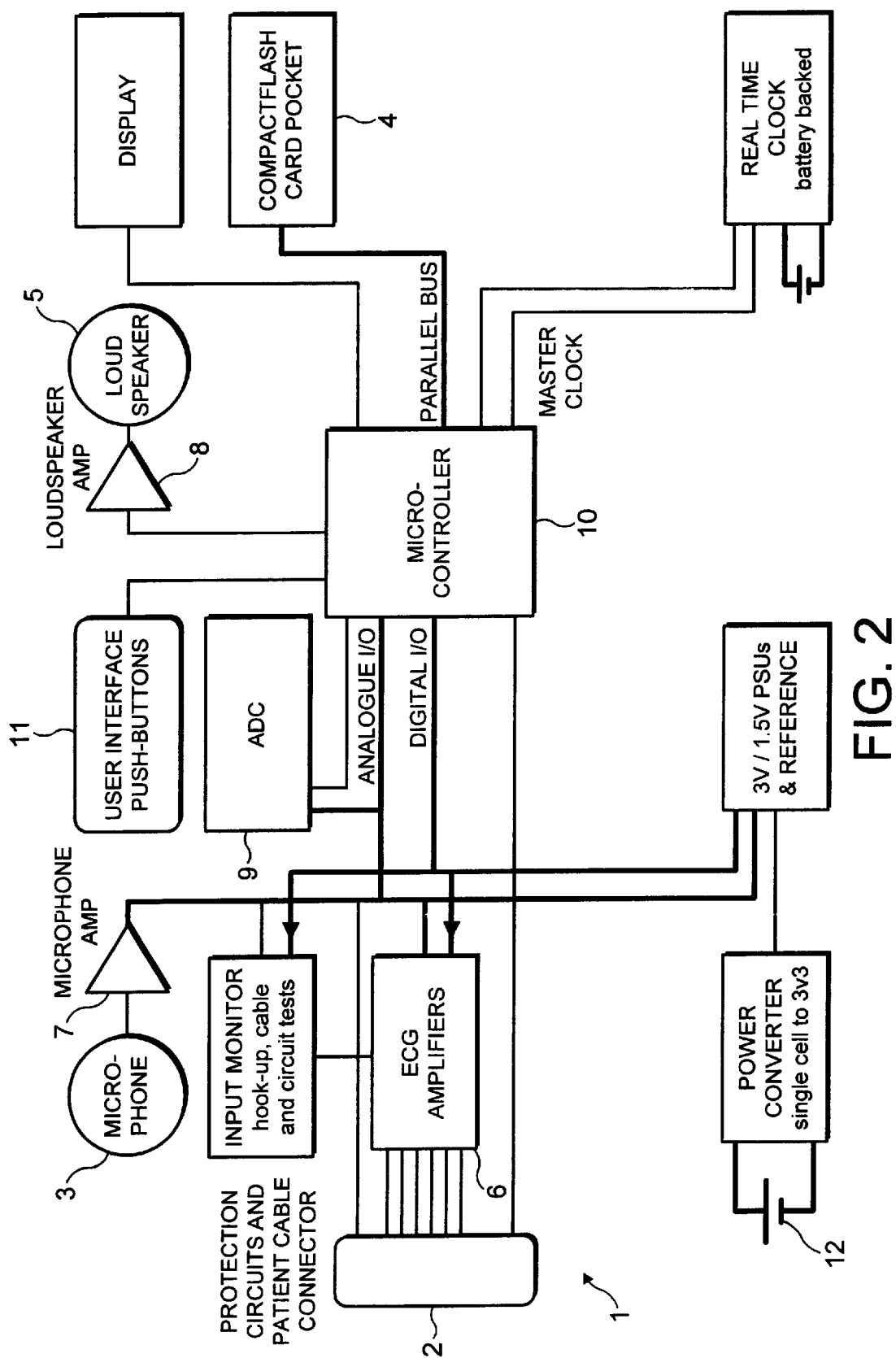

For a better understanding of the present invention, specific embodiments will now be described by way of example, with reference to the accompanying drawings, in which:

FIG. 1 shows body monitoring apparatus according to the invention connected to ECG electrodes; and FIG. 2 shows a schematic circuit design of body monitoring apparatus according to the invention.

Referring to the embodiment in FIGS. 1 and 2, portable ECG recording apparatus 1 includes a port 2 for connection to ECG electrodes 14, a microphone 3 for detecting a sound signal, a solid state memory card 4 and a loudspeaker 5. The apparatus 1 also includes processing electronics which include amplifiers 6, 7, 8, an analogue to digital converter (ADC) 9 and a microprocessor 10.

ECG electrodes 14 are attached to the patient's body to detect physiological information, and are connected via port 2 to ECG recording apparatus 1.

Prior to recording physiological information, the clinician activates the microphone 3 using the user interface controls 11, which causes the processing electronics to provide power to the microphone 3 from a battery 12. Vocal signals from the clinician are detected by the microphone 3, and the analogue signals are fed through the microphone amplifier 7. The amplified signals are digitised using the ADC 9 and stored on the memory card 4. The vocal recording may be compressed in order to save storage space on the memory card. An LCD display 13 displays user options and system status.

The clinician is able to replay the vocal recording if desired, and if it is not suitable it may be re-recorded. In order to replay the vocal recording, the digitised signal is reconstructed including being passed through the loudspeaker amplifier 8, and is acoustically output through the loudspeaker 5. The microprocessor 10 deactivates the loudspeakers when not in use to save power.

The clinician is therefore able to make a vocal recording to store any information which is relevant to the subsequent physiological data recording. This method of data input provides a very simple and practical method for the clinician without recourse to a keyboard or a large number of button operations. Once the clinician is satisfied with the vocal recording, the microphone 3 may be deactivated in order to lower the power requirements.

The microphone 3 device characteristics may vary depending on the requirements, for example with the acoustic input level set so the device can record speech clearly at a distance of 10–30 cm from the clinician's mouth. In the embodiment, the microphone response is +/− 3 dB over the range 600 Hz to 2 kHz. The speech signal is sampled and recorded at 8 kHz.

The loudspeaker may have any suitable characteristics required, for example the acoustic output capability of 70 dBA, 10 cm from the output port. The loudspeaker response in the embodiment is +/−10 dB over the range 600 Hz to 3 kHz.

Physiological signals detected by the sensors are fed through ECG amplifiers 6 and digitised using the same analogue to digital converter 9 as is used to digitise the vocal signal. The digitised physiological data is stored on the memory card 4, which is the same storage medium as the vocal recording. Thus, the memory card 4 contains recordings of both the vocal signal and the physiological data and these will be kept together, even if the data is transferred to a remote site and the files cannot become accidentally separated.

Since both the vocal signal and ambulatory recording are stored on the same storage medium, this provides a unique identification scheme for the recording. If the data is sent to a remote site, it is possible to identify both the recording and its source using the information held in the vocal recording. Physiological symptoms and medication details may also be relayed if these have been recorded. In the case of trans-telephonic event recording, the message can be chosen by the clinician to satisfy any identification requirements of the receiving station. The message allows the receiving station to automatically identify the patient and therefore the system can react to the physiological data that will follow in the most appropriate manner. This avoids relying on the patient to perform this function. This advantageously minimises patient interaction, which may be important if the patient is in distress, avoiding the time required to teach the patient the appropriate responses, and avoiding any error caused by patient confusion or misinterpretation of patient's speech.

In the embodiment, the loudspeaker can also replay sound recordings previously stored in the apparatus. These recordings may be supplied, for example, by the device manufacturer, uploaded from a personal computer or recorded directly on the recorder. The loudspeaker can output pre-recorded vocal signals, or sound signals (beeps) indicating successful/failed operations, button pushes or self-diagnostic error messages. For example, vocal messages from the recorder may be triggered on the basis of the recorder status. These include requesting the clinician to check recording inputs before starting recording, warning that a sensor is not connected, or prompting a change in battery.

In the embodiment, the recorder incorporates an analysis system where automatically detected physiological conditions will trigger the replay of an appropriate vocal recording prompting the patient to certain actions. These may be, for example, downloading of data or contacting a doctor.

Although in the embodiment, the storage medium is a solid state memory card, any other suitable storage medium may be used instead.

What is claimed is:

1. A method of monitoring physiological information, the method including:
   detecting and recording physiological information from a human or animal subject using at least one physiological sensor;
   detecting and recording a vocal signal using an acoustic sensor, the vocal signal including a component suitable for identification of the human or animal subject of the recording, wherein a vocal recording is stored on a same storage medium as the physiological information and wherein only one such vocal signal is stored within the storage medium such that the stored vocal signal acts as a unique acoustic identification label for the physiological information stored within the storage medium.

2. A method according to claim 1, wherein the vocal recording contains a component suitable for the identification of at least one of the physician, clinician, hospital, clinic, and company for whom the monitoring is performed.

3. A method according to claim 1, wherein the vocal recording is a primary means of identifying the human or animal subject of the recording.

4. A method according to claim 1, wherein the vocal recording is a primary means of identifying at least one of the physician, clinician, hospital, clinic, and company for whom the monitoring is performed.

5. A method according to claim 1, where the vocal recording is made before or after, not concurrent with, the recording of the physiological information.

6. A method according to claim 1, including the step of replaying the vocal recording once made, and overwriting the vocal recording with a new vocal recording if the initial vocal recording is not considered to be adequate.

7. A method according to claim 1, including a step wherein power is supplied to the acoustic sensor only when a vocal recording is to be made.

8. A method according to claim 1, including a step wherein power is restricted from the acoustic sensor when a vocal recording is not being made.

9. A method according to claim 1, further including transmitting both a recorded physiological information and the vocal signal to a remote location in such a manner that the vocal signal is directly associated with the transmitted recorded physiological information such that transmitted vocal signal acts as an acoustic identification label for the transmitted physiological data.

10. A method according to claim 9, wherein the transmitted vocal signal is a primary means of identifying the human or animal subject of the physiological information recording.

11. A method according to claim 9, wherein the transmitted vocal signal is the primary means of identifying at least one of the physician, clinician, hospital, clinic, and company for whom the monitoring is performed.

12. A method according to claim 9, wherein the vocal recording is transcribed and said transcription is used to label the transmitted physiological recording, by associated storage of the transcribed data with the physiological recording.

13. A method according to claim 1, wherein an additional component of the vocal recording is used to define the method of data analysis that should be applied to the recorded physiological information.

14. Body monitoring apparatus including: processing electronics for receiving and recording on a storage medium physiological information from a human or animal subject using at least one physiological sensor; processing electronics for receiving and recording a vocal signal from an acoustic sensor, the vocal signal including a component suitable for the identification of the human or animal subject of the recording;
   processing electronics for storing the vocal signal onto the same storage medium as used to store the physiological information; processing electronics for ensuring that only one vocal signal is stored within the storage medium, such that the stored vocal signal acts as a unique acoustic identification label for the physiological information stored within the storage medium.

15. Apparatus according to claim 14, wherein the vocal recording contains a component suitable for the identification of at least one of the physician, clinician, hospital, clinic, and company for whom the monitoring is performed.

16. Apparatus according to claim 14, wherein the vocal recording is a primary means of identifying the human or animal subject of the recording.

17. Apparatus according to claim 14, wherein the vocal recording is the primary means of identifying at least one of the physician, clinician, hospital, clinic, and company for whom the monitoring is performed.

18. Apparatus according to claim 14, where the vocal recording is made before or after, not concurrent with, the recording of the physiological information.

19. Apparatus according to claim 14, including a loudspeaker and processing electronics such that the vocal recording, or a previously stored sound signal, may be replayed through the loudspeaker.

20. Apparatus according to claim 14, the processing electronics adapted for supplying power to activate the acoustic sensor only when a vocal recording is to be made.

21. Apparatus according to claim 14, the processing electronics adapted for restricting power to deactivate the acoustic sensor when a vocal recording is not being made.

22. Apparatus according to claim 14, comprising means to transmit both the recorded physiological information and a recorded vocal signal to a remote location in such a manner that these recordings are directly associated with each other.

23. A method of monitoring physiological information according to claim 1, wherein a new vocal signal acquired automatically overwrites the previously stored vocal signal such that only one stored vocal signal containing the subject identified component can be stored within the storage medium at any time.

24. A method of monitoring physiological information according to claim 1, wherein the vocal signal recording contains a component adapted to define a method of data analysis that is to be applied to the stored physiological information.

25. A method according to claim 1, wherein the vocal signal recording and the physiological recording are stored as associated data and the vocal signal recording is used directly as an acoustic label for the physiological recording.

26. A method according to claim 10, wherein the transmitted vocal signal contains a component suitable for the identification of at least one of a doctor, clinician, hospital, clinic and company conducting said recording procedure.

27. A method according to claim 9, wherein at last part of the vocal recording is transcribed and said transcription is used to label the transmitted physiological recording, by at least one of appended data, prefixed data and encoded data within the stored physiological recording.

28. Apparatus according to claim 6, further including:
processing electronics for automatically overwriting a previously stored local signal on acquiring a new vocal signal such that only one stored vocal signal containing the subject identification component can be stored within the storage medium at any time.

* * * * *